United States Patent [19]
Carter

[11] Patent Number: 6,090,067
[45] Date of Patent: *Jul. 18, 2000

[54] SURFACE ACCESS HEMOSTATIC VALVE

[76] Inventor: Bruce C. Carter, 4034 Copeland Rd., Tyler, Tex. 75701

[ * ] Notice: This patent is subject to a terminal disclaimer.

[21] Appl. No.: 09/099,620

[22] Filed: Jun. 18, 1998

Related U.S. Application Data

[63] Continuation-in-part of application No. 09/026,378, Feb. 19, 1998.

[51] Int. Cl.[7] .................................................... A61M 11/00
[52] U.S. Cl. ............................................ 604/93; 604/256
[58] Field of Search ................................ 604/93, 41, 256, 604/246, 247, 264, 523, 539, 175, 500, 502; 600/36

[56] References Cited

U.S. PATENT DOCUMENTS

| | | | |
|---|---|---|---|
| 4,496,349 | 1/1985 | Cosentino | 604/175 |
| 4,832,054 | 5/1989 | Bark | 128/899 |
| 5,807,356 | 9/1998 | Finch, Jr. et al. | 604/284 |

*Primary Examiner*—Wynn Wood Coggins
*Assistant Examiner*—Deborah Blyveis
*Attorney, Agent, or Firm*—Michael A. O'Neil

[57] ABSTRACT

A surface access hemostatic valve comprises a tube and a hemostatic valve mounted at the distal end of the tube for positioning at the surface of the skin of the patient. The graft having the surface access hemostatic valve mounted thereon is surgically installed in the skin of the patient. Thereafter the interior of the tube is sterilized and an access member is inserted through the hemostatic valve, through the tube, and into the interior of the graft.

1 Claim, 14 Drawing Sheets

SURFACE ACCESS HEMOSTATIC VALVE

CROSS REFERENCE TO RELATED APPLICATION

This application is a continuation-in-part of prior application Ser. No. 09/026,378, filed Feb. 19, 1998, currently pending.

TECHNICAL FIELD

This invention relates generally to grafts of the type used in various medical applications including hemodialysis, and more specifically to an improved apparatus for and method of accessing medical grafts.

BACKGROUND AND SUMMARY OF THE INVENTION

Various medical procedures, including in particular hemodialysis, involve the surgical installation of one or more grafts to facilitate access to the blood flow of the patient. Currently hemodialysis patients undergo repetitive, often painful large needle punctures of their skin and underlying tissue numerous times per week to gain entry into such grafts. The disadvantages of this approach are numerous and well documented. Hematomas can result from uncontrolled bleeding. The graft is damaged by the multiple puncture technique leading ultimately to poor and inadequate functioning or thrombosis resulting in the need for additional operations, replacement of the graft and resultant tissue trauma. Temporary access through internal jugular veins or other venous access sites further adds to patient morbidity.

Significant technical expertise and nursing care is currently required to puncture the grafts. Following the procedure and needle removal, skilled nursing staff are required to hold pressure on the graft puncture site for variable periods of time which not infrequently last up to an hour, or more.

The present invention comprises a surface access hemostatic valve for medical use which overcomes the foregoing and other problems long since associated with the prior art. In accordance with the broader aspects of the invention, a surface access hemostatic valve includes a tube connected in fluid communication with a graft and extending from the graft to a hemostatic valve situated at the outer surface of the skin of the patient. Access to the blood flow of the patient is achieved by inserting an instrument through the hemostatic valve through the tube and into the graft.

The advantages obtained by means of the invention include the following:

1. Decreased patient suffering.

2. Increased patient comfort and satisfaction.

3. No needle damage to the graft.

4. Longer lifetime of the graft.

5. Decreased number of surgical procedures in the lifetime of the patient.

6. Decreased cost of medical care.

7. Improved graft functioning with greater flow rates and decreased procedure time.

8. Decreased nursing staff time without difficult, highly skilled punctures having to be performed.

9. Decreased post procedure time with no requirement for applying pressure at the puncture site to control bleeding.

10. Further potential for improving graft design by strengthening the material used as graft punctures are no longer required.

11. Decreased number of graft-related complications for patients undergoing long-term care with fewer hematomas (therefore less associated vein, nerve, and arterial compression with less deep venous thrombosis and decreased potential for decreased use of the extremity), less potential for arterial embolic disease, less exposure to the risks of anesthesia with decreased need for surgical intervention or radiologic declot intervention.

12. Decreased damage to the entire venous system of the patient with decreased need for temporary access to other large caliber veins because of graft malfunction.

13. Safe and efficient access for monitoring the graft to prevent significant stenoses and occlusions.

14. Facilitates endoluminal placement of a short segment graft extension without damage to the existing graft.

15. Allows less intensively trained personnel to take care of patients.

16. Safe and easy access for administering thrombolytic agents to dissolve clots that develop in grafts.

BRIEF DESCRIPTION OF THE DRAWINGS

A more complete understanding of the invention may be had by reference to the following Detailed Description when taken in conjunction with the accompanying Drawings, wherein.

DETAILED DESCRIPTION

Referring now to the Drawings, and particularly to FIGS. 1, 2, 3, and 4 thereof, there is illustrated a currently utilized technique for gaining access to medical grafts of the type used in hemodialysis and similar procedures. In accordance with current practice, a graft or fistula 20 is installed beneath the skin 22 of a patient P. The graft 20 is connected between an artery or a vein of the patient and is utilized to provide access to the blood flow of the patient during the procedure.

Figure 1:
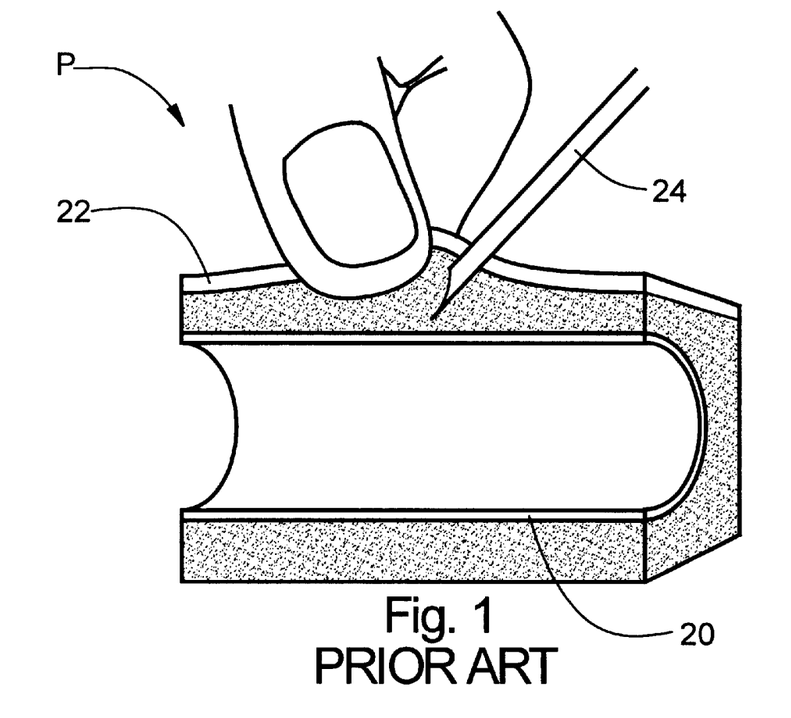
FIG. 1 is a diagrammatic illustration of an initial step of a prior art technique for gaining access to a hemodialysis graft in order to effect hemodialysis.
Figure 2:
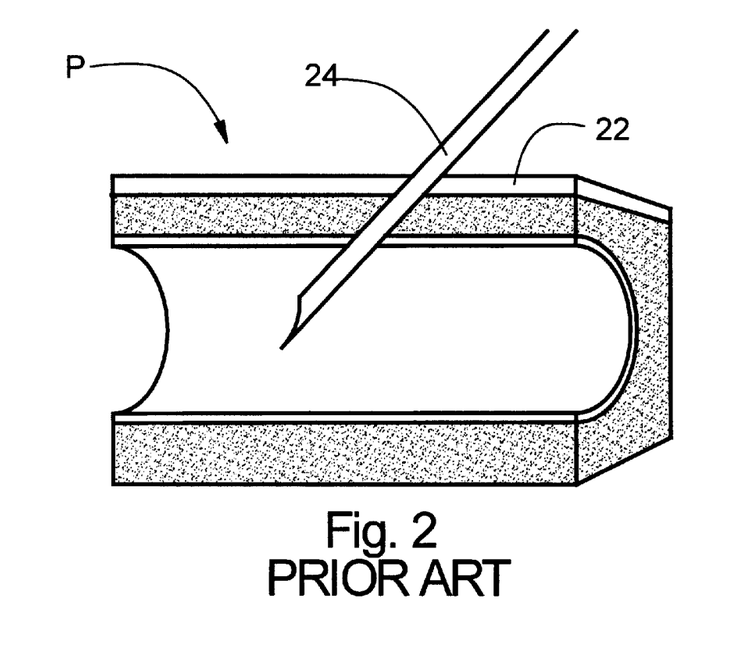
FIG. 2 is a diagrammatic illustration of a subsequent step in the technique of FIG. 1.

The skin 22 of the patient P is first "tented" as illustrated in FIG. 1, and a needle 24 is inserted therethrough. The needle 24 is preferably inserted through the skin 22 of the patient P at an angle of 45°. As is illustrated in FIG. 2, further insertion of the needle 24 causes the needle to penetrate the graft 20, again at an angle of 45°. As will be understood by reference to FIGS. 1 and 2, the needle 24 is inserted through the skin 22 and the graft 20 with the tip thereof pointed down. Following insertion of the needle through the graft, the needle is rotated 180° so that the tip thereof is pointed up. Insertion of the needle continues until the hub 26 of the needle 24 engages the skin 22 of the patient P as illustrated in FIG. 3.

Figure 3:
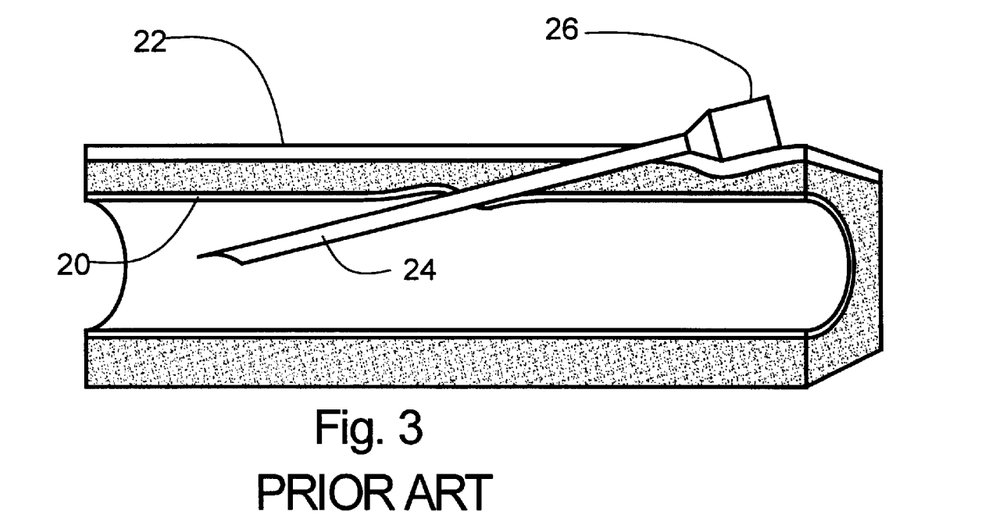
FIG. 3 is a diagrammatic illustration of a still later step in the technique of FIG. 1.
Figure 4:
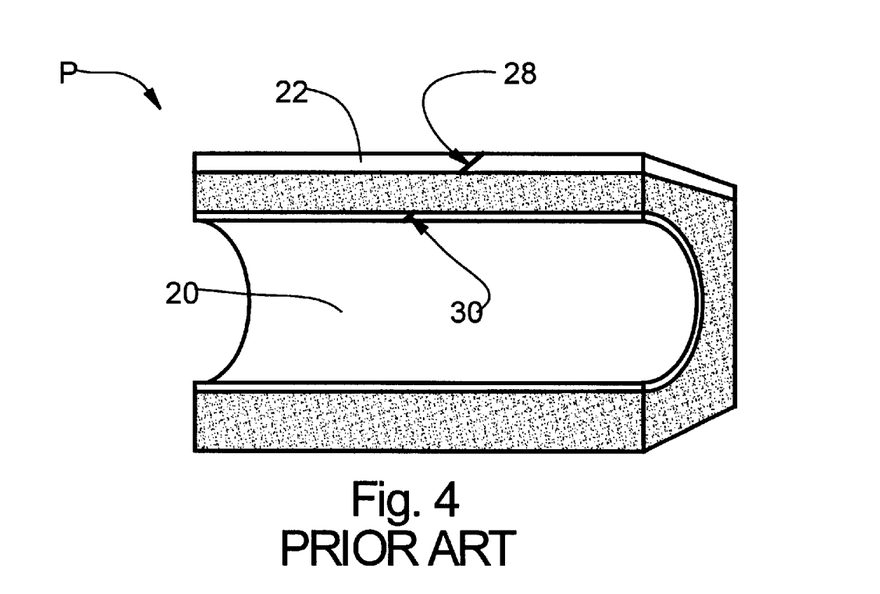
FIG. 4 is a diagrammatic illustration of the successful completion of the technique of FIG. 1.
Figure 5:
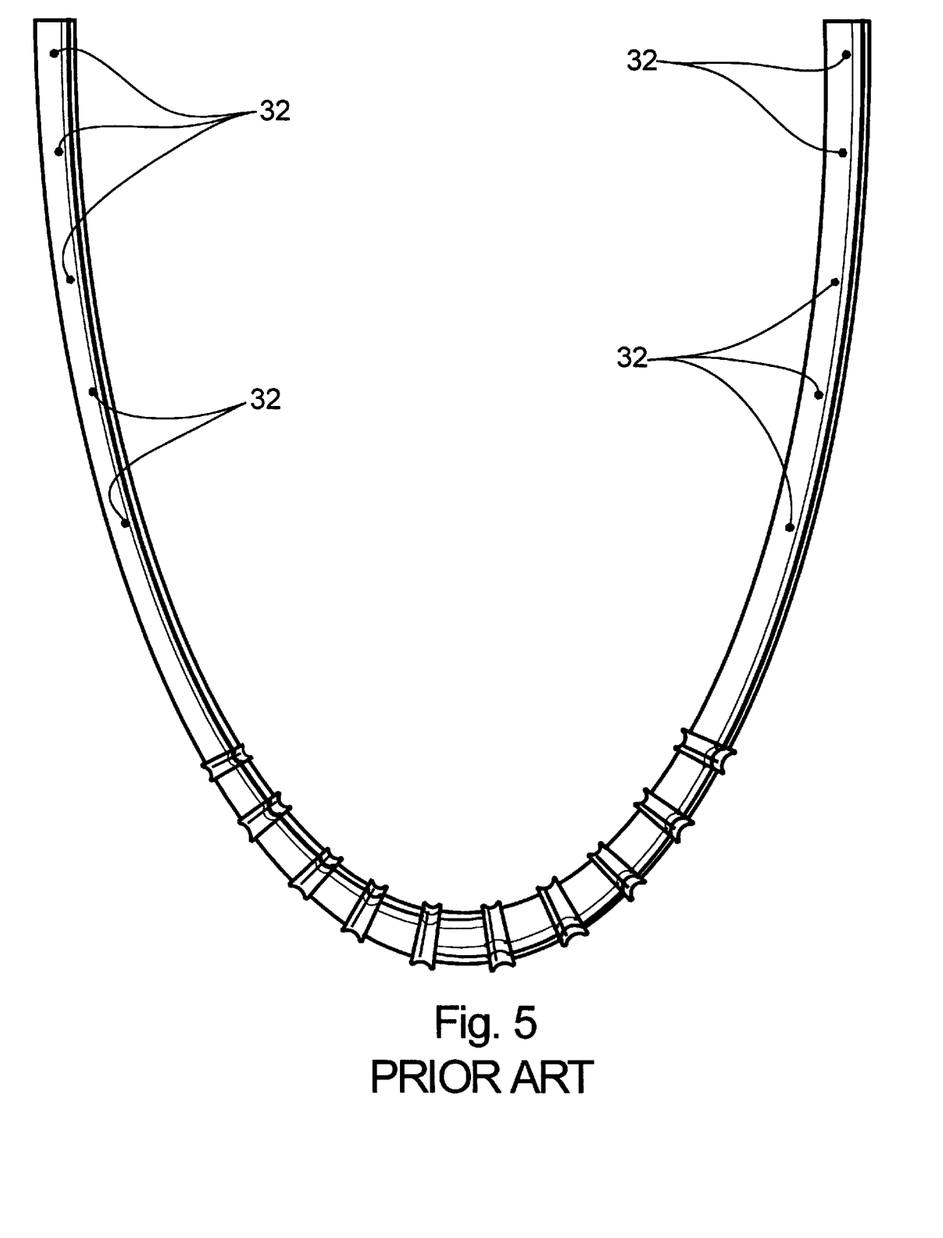
FIG. 5 is a illustration of a prior art hemodialysis graft.

When the needle 24 has been inserted as illustrated in FIG. 3 the medical procedure begins and continues for a predetermined period of time as prescribed by the attending physician. When the procedure is complete, the needle 24 is withdrawn from the graft 20 and the skin 22 in the usual manner. Assuming that the needle 24 has been properly inserted through the skin 22 and the graft 20, the point of penetration through the skin 28 and point of penetration through the graft 30 will be misaligned following withdrawal of the needle as illustrated in FIG. 4. This is advantageous in reducing the possibility of bleeding through the graft and the skin following the procedure. Nevertheless it is necessary to maintain pressure on the point of penetration 28 to avoid bleeding. Referring to FIG. 5, the graft 20 is illustrated in further detail. In FIG. 5 the graft 20 is provided with a plurality of hypothetical reference points 32 each located one centimeter from the next adjacent reference point. As is suggested by the reference points 32, in the practice of the currently used hemodialysis technique, the needle is not inserted at the same location preparatory to successive procedures. Instead, the sites of successive needle penetrations into the graft 20 are separated by at least one centimeter. This is to reduce the possibility of pseudoaneurysm at the needle insertion site, and also to reduce the possibility of early graft failure.

As will perhaps be apparent from the foregoing brief discussion from currently used techniques, the state of the art is characterized by patient dissatisfaction, discomfort, and suffering due to the necessity of frequent needle insertions through the skin of the patient. A parallel problem is reduction of the anticipated life of the graft due to repeated needle insertions therethrough. This leads to an increased number of surgical procedures over the lifetime of the patient in order to replace failed grafts which in turn leads to significant increases in the cost of treatment. Thus, a need exists for improvements in the art and practice of medical procedures such as hemodialysis with a view toward significant reductions in the foregoing problems.

Figure 6:
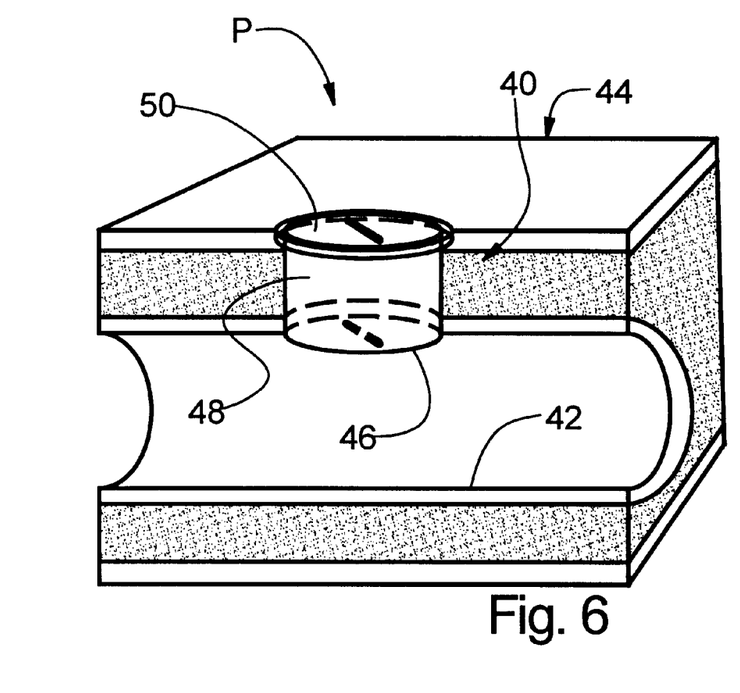
FIG. 6 is a diagrammatic illustration of an apparatus and method comprising a first embodiment of the present invention.

Referring now to FIG. 6, there is shown a surface access double hemostatic valve 40 comprising the present invention. In accordance with the invention, an otherwise conventional medical graft or fistula 42 is inserted beneath the skin 44 of a patient P utilizing conventional surgical techniques. A first hemostatic valve 46 is secured in the wall of the graft 42. A chamber 48 extends outwardly from the hemostatic valve 46 through the skin 44 of the patient P. A second hemostatic valve 50 is located at the distal end of the chamber 48 and is mounted parallel to the surface of the skin 44 of the patient. As will be understood by those skilled in the art, the use of the present invention facilitates access to the interior of the graft 42 through the double hemostatic valve 40 without requiring the insertion of needles through the skin 44 and the graft 42.

Figure 7:
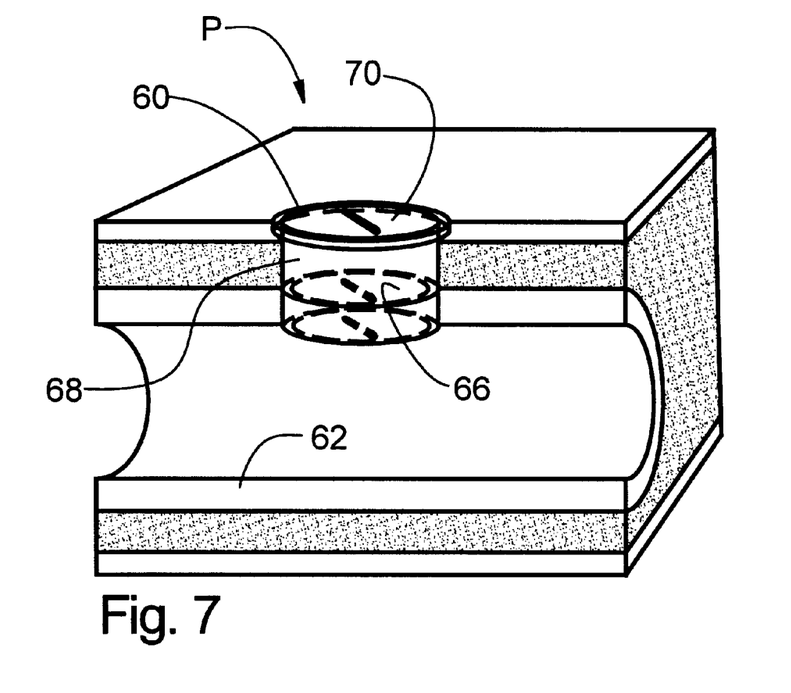
FIG. 7 is a detailed illustration of an apparatus and method comprising a second embodiment of the present invention.
Figure 8:
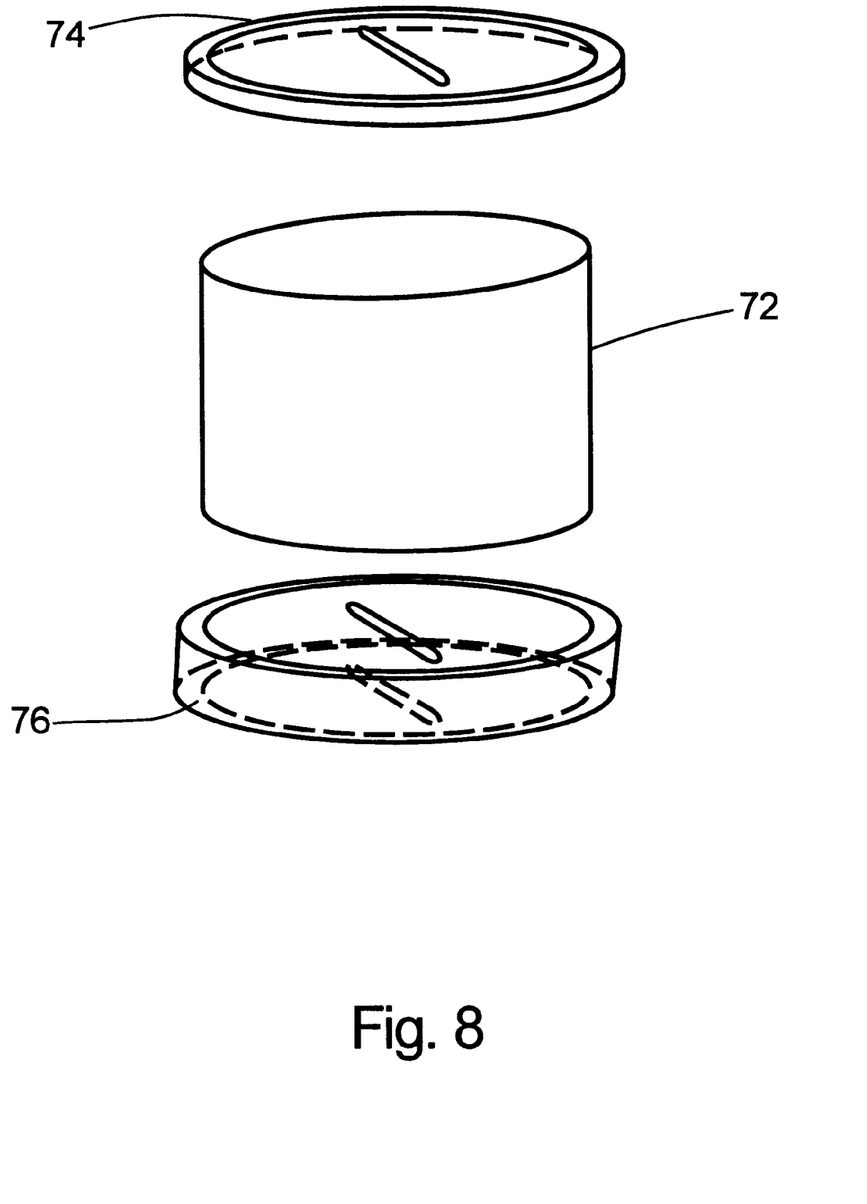
FIG. 8 is an exploded view further illustrating the method and apparatus of FIG. 7.

FIGS. 7 and 8 illustrate a second embodiment of the invention. Again, a double hemostatic valve 60 is secured to a graft 62 and extends therefrom to the surface of the skin 64 of the patient P. The valve 60 includes a first hemostatic valve 66 secured in the graft 62, a chamber 68 extending from the valve 66, and a second hemostatic valve 70 located at the surface of the skin of the patient P.

As is best illustrated in FIG. 8, the valve 60 of FIG. 7 differs from the valve 40 of FIG. 6 in that the valve 66 of the valve 60 comprises a double thickness hemostatic valve 72 mounted between two wafers 74 and 76. The wafers 74 and 76 are preferably mounted within the wall of the graft 62 and comprise either a suitable metal, such as stainless steel, or a suitable plastic material.

FIGS. 6, 7, and 8 illustrate first and second embodiments of the invention each comprising double hemostatic valves. It will be understood, however, that the invention can be practiced using a single hemostatic valve located at the surface of the skin of the patient in whom the graft is installed.

Figure 9:
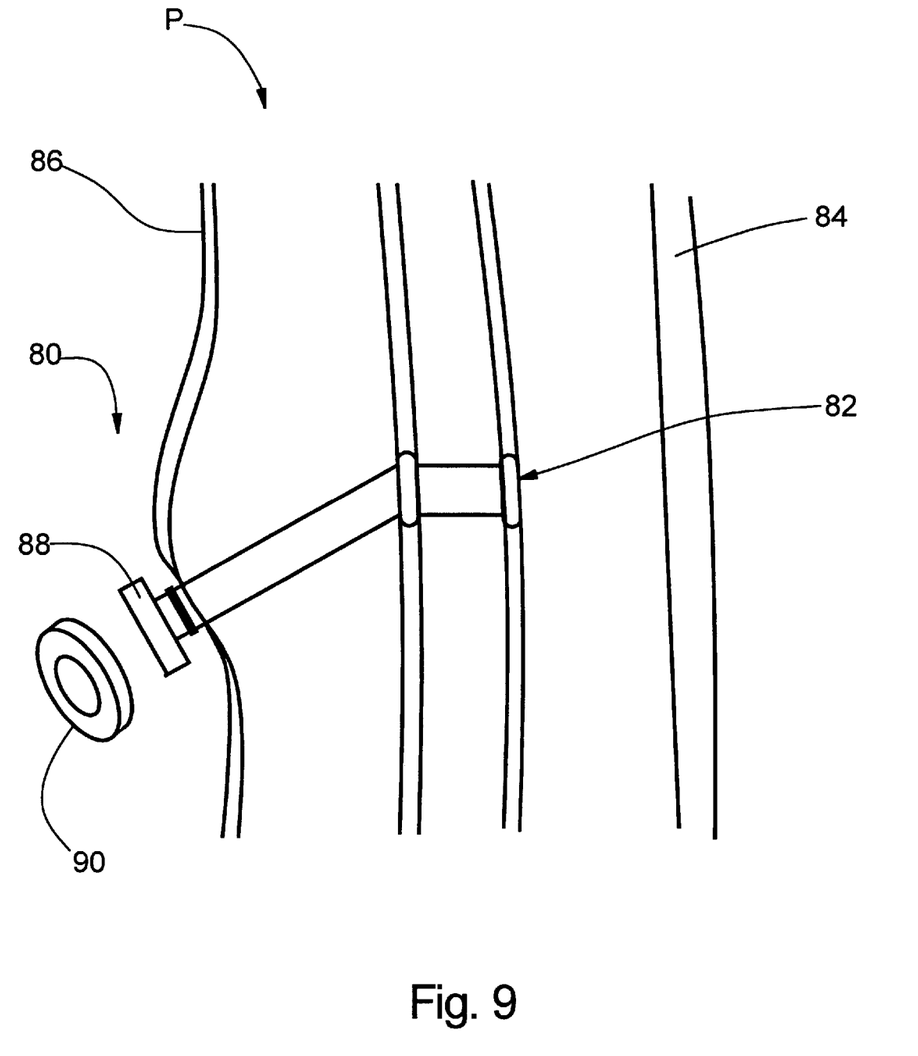
FIG. 9 is a further illustration of the method and apparatus of the present invention.

Referring to FIG. 9, there is shown a surface access double hemostatic valve 80 comprising the present invention. The valve 80 may be constructed similarly to the valve 40 of FIG. 6 or to the valve 60 of FIGS. 7 and 8 and includes a first hemostatic valve 82 secured in the wall of a graft 84 installed beneath the surface of the skin 86 of a patient P. The valve 80 further includes a second hemostatic valve 88 located at the surface of the skin of the patient P to provide access to the interior of the graft 84. A sealing cap 90 can be provided for secure engagement with the valve 88 and would normally be retained in engagement with the valve except during the time that the valve 80 is in use. The purpose of the sealing cap 90 is to prevent contamination of the surface access double hemostatic valve 80 by contact with foreign agents.

Figure 10:
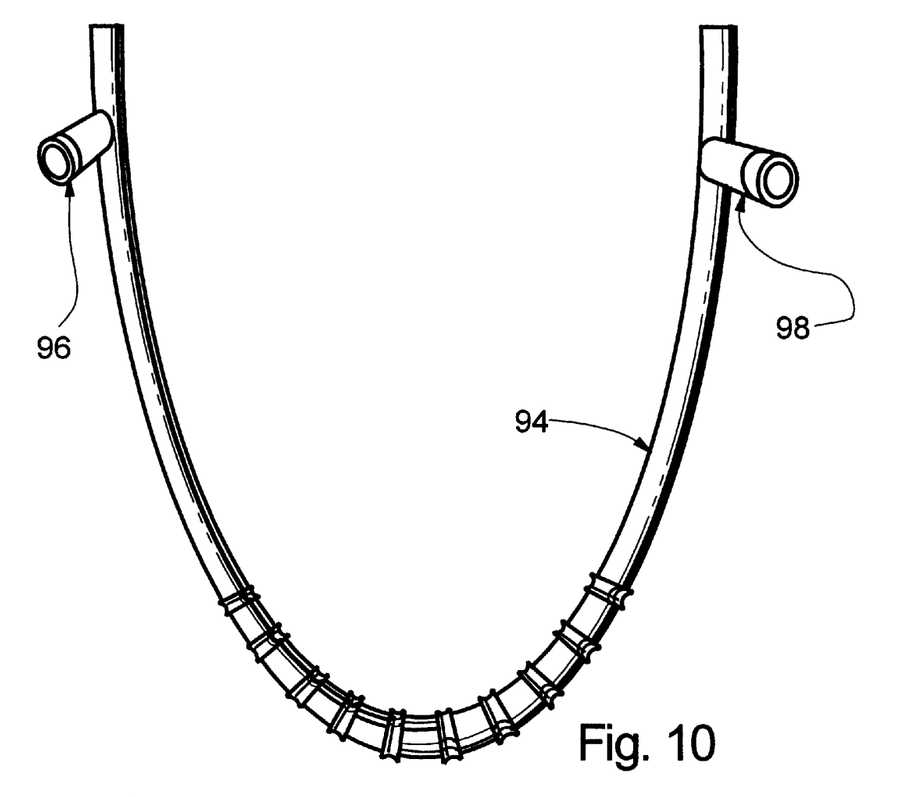
FIG. 10 is an illustration of a hemodialysis graft equipped with the apparatus of the present invention.

FIG. 10 illustrates a graft 94 having surface access double hemostatic valves 96 and 98 mounted thereon at spaced apart locations. The valves 96 and 98 may be constructed similarly to the valve 40 illustrated in FIG. 6. Alternatively, the valves 96 and 98 may be constructed similarly to the valves 60 illustrated in FIGS. 7 and 8. In either case, the valves 96 and 98 may be provided with sealing caps of the type illustrated in FIG. 9.

Figure 11:
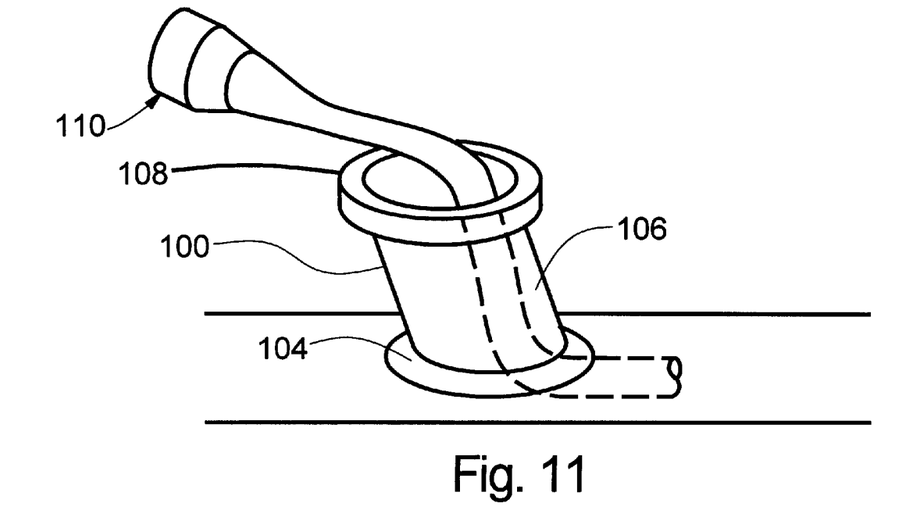
FIG. 11 is a further illustration of the method of the present invention.

Referring now to FIG. 11, there is shown a surface access double hemostatic valve 100 incorporating the present invention. The valve 100 is utilized in conjunction with an otherwise conventional graft 102 and may be constructed similarly to the valve 40 of FIG. 6, or the valve 60 of FIGS. 7 and 8, or the valve 80 of FIG. 9. As will be appreciated by reference to the foregoing FIGURES, the valve 100 includes a first hemostatic valve 104 which is secured in the wall of the graft 102, a chamber 106 extending from the valve 104, and a second hemostatic valve 108 located at the surface of the skin of the patient.

After the graft 102 and the valve 100 have been installed, the interior of the chamber 106 is flushed with a heparinized saline solution. Thereafter, an introducer set sheath 110 is inserted through the valve 108, the chamber 106, and the valve 104 and into the interior of the graft 102. By this means, access to the blood of the patient flowing through the interior of the graft 102 is provided without the necessity of penetrating the skin of the patient and the graft located therein with a needle.

Figure 12:
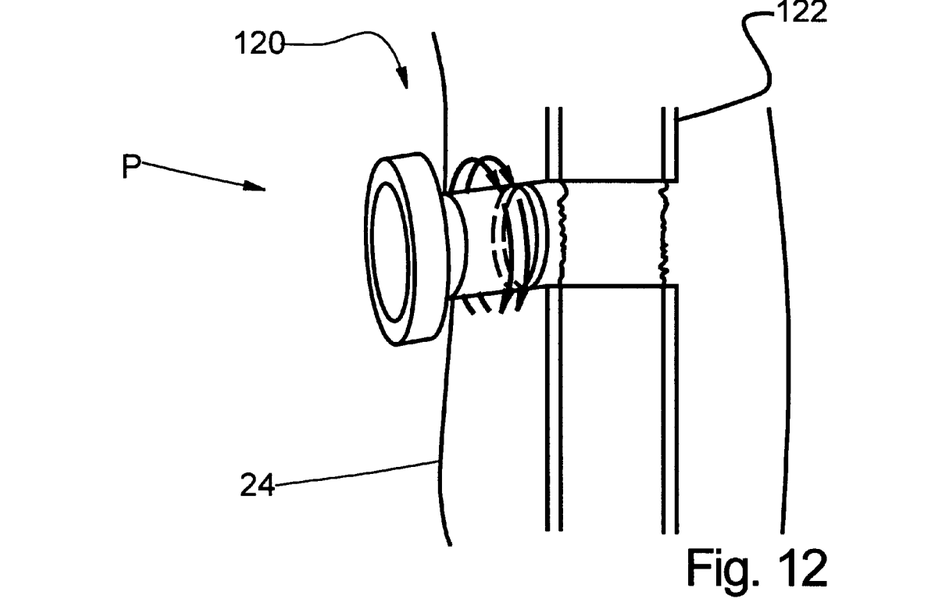
FIG. 12 is an illustration of a first step in an alternative method according to the present invention.
Figure 13:
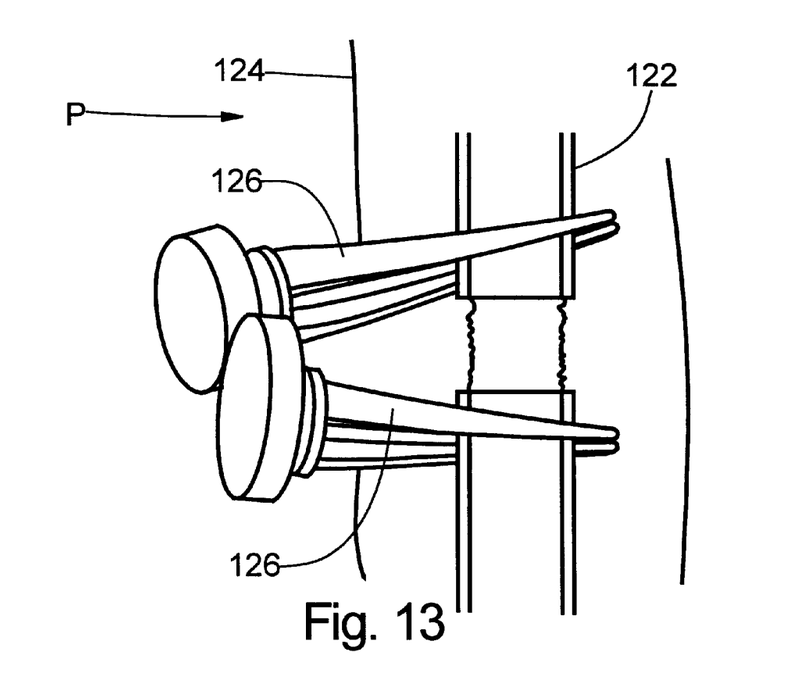
FIG. 13 is an illustration of a later step in the alternative method of the present invention.
Figure 14:
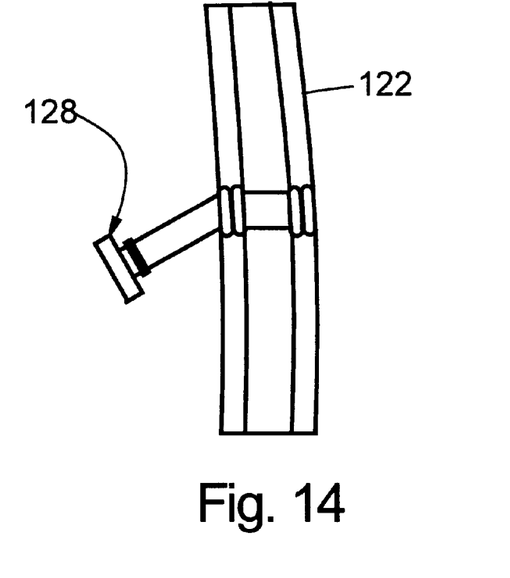
FIG. 14 is an illustration of the completion of the alternative method of the present invention.

FIGS. 12, 13, and 14 illustrate an aspect of the present invention which facilitates the replacement of the surface access double hemostatic valve of the present invention utilizing simple local anesthetic based techniques. FIG. 12 illustrates a surface access double hemostatic valve 120 which for whatever reason requires replacement. The valve 120 is secured to and mounted in fluid communication with a graft 122 which has previously been installed beneath the surface of the skin 124 of a patient P utilizing conventional surgical techniques. To accomplish replacement of the valve 120, a local anesthetic is administered to the patient P again utilizing conventional techniques. Thereafter, the graft 122 is sealed utilizing temporary clamps 126, and the valve 120 is removed. Thereafter a new lock-in double hemostatic valve 128 is secured in the wall of the graft 122 and the clamps 126 are removed. At this point the valve 128 and the graft 122 are arranged as illustrated in FIG. 14. The use of the valve 128 is the same as described hereinabove in conjunction with the valves 40, 60, and 80.

Figure 15:
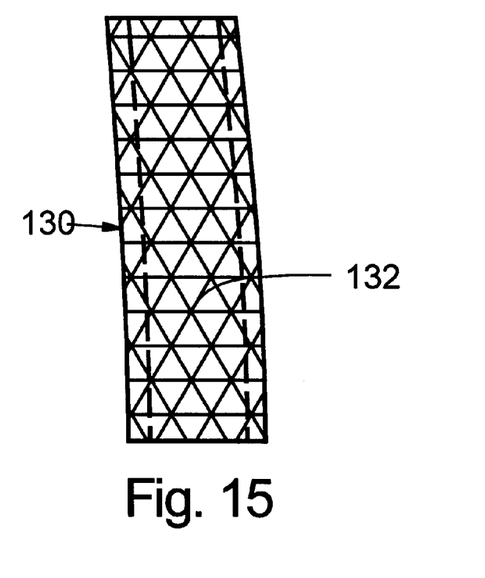
FIG. 15 is a diagrammatic illustration of a first improved graft according to the present invention.
Figure 16:
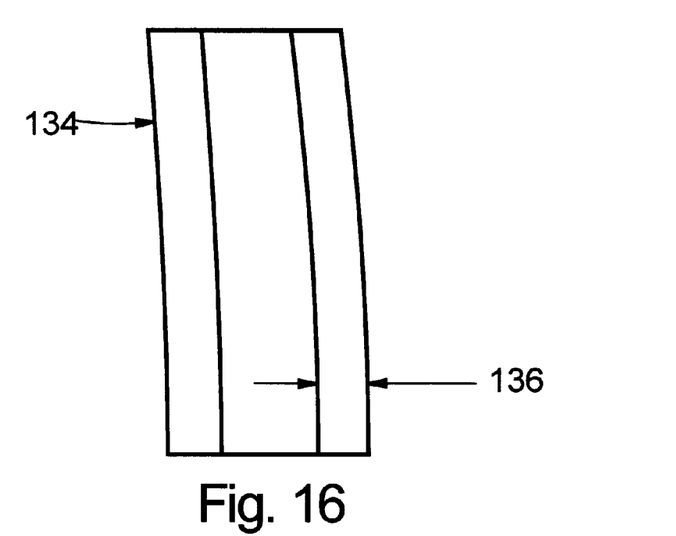
FIG. 16 is a diagrammatic illustration of a second improved graft according to the present invention.

FIGS. 15 and 16 illustrate alternative hemodialysis graft designs which may be utilized in the practice of the invention. In FIG. 15, an otherwise conventional medical graft 130 is reinforced by a metal stent 132. In FIG. 16 there is illustrated an otherwise conventional medical graft 134 having a substantially increased wall thickness 136. As will be appreciated by those skilled in the art, grafts having reinforced and/or extra thick walls cannot be used in the practice of conventional graft access techniques due to the inherent difficulty of inserting a needle therethrough. Conversely, such improved graft designs are readily adapted to the practice of the present invention which does not require the insertion of a needle through the wall of the graft.

Figure 17:
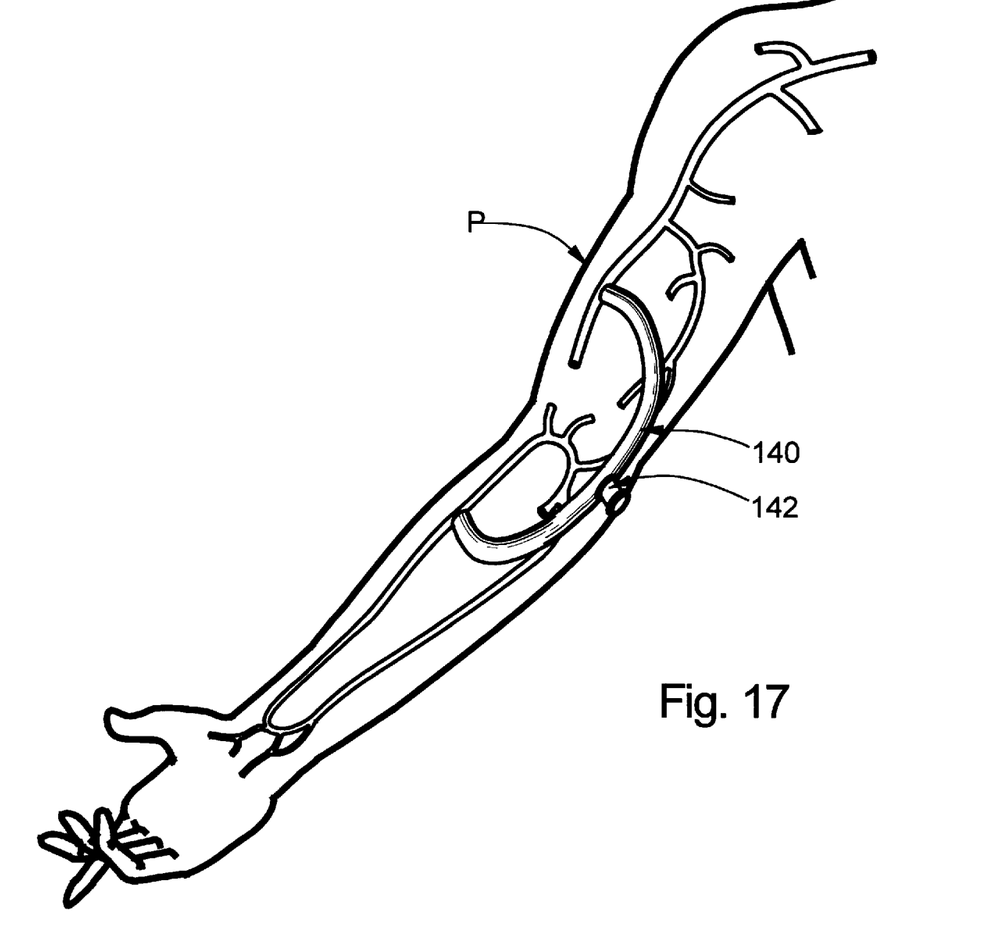
FIG. 17 is a diagrammatic illustration of an apparatus and method comprising a third embodiment of the present invention.

Referring now to FIG. 17, a third embodiment of the apparatus and method of the present invention is illustrated. A graft 140 comprising an arteriovenous (A-V) fistula is connected between an artery and a vein of a patient P. It will be understood that although the graft 140 is illustrated in FIG. 17 as being installed in the arm of the patient P, the present invention is fully applicable to other graft locations. The graft 140 is implanted within the patient P and is connected between an artery and a vein of the patient P utilizing conventional surgical techniques.

The graft 140 is provided with a surface access hemostatic valve 142 comprising the present invention. The valve 142 extends between the body of the graft 140 and the surface of the skin of the patient P. The purpose of the valve 142 is to eliminate or greatly reduce the necessity of puncturing the graft 140 with a needle.

Figure 18:
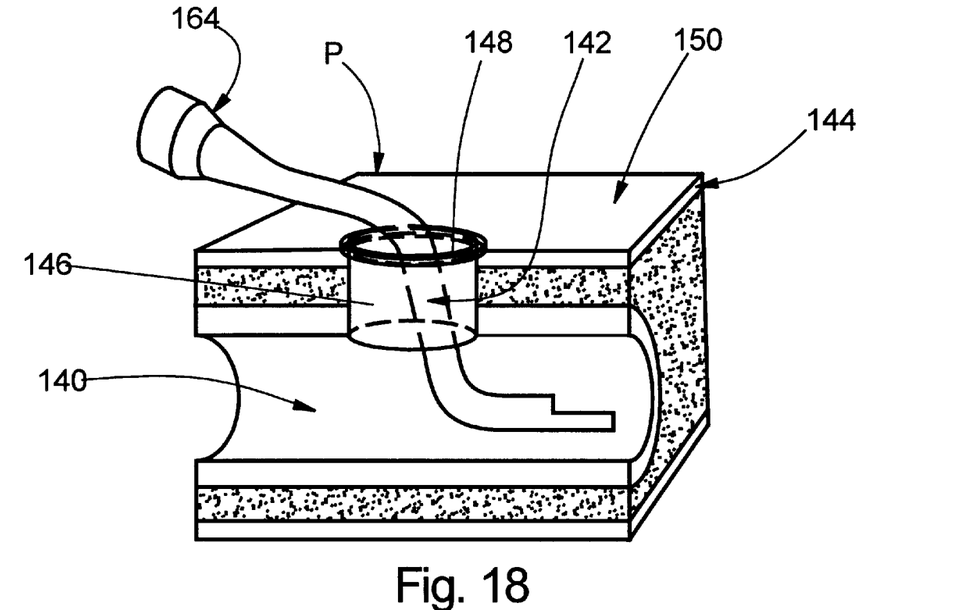
FIG. 18 is a further illustration of the method and apparatus of FIG. 17.

The graft 140 and the surface access valve 142 are further illustrated in FIG. 18. The graft 140 is installed beneath the skin 144 of the patient P in accordance with conventional techniques. The valve 142 includes a passageway 146 comprising a tube formed from polytetrofloroethylene, expanded polytetrofloroethylene, or other, similar materials suitable for use in medical applications. The tube 146 extends between the interior of the graft 140 and a hemostatic valve 148 located at the surface 150 of the skin 144 of the patient P. Thus, the valve 142 differs from the valves illustrated in FIGS. 6, 7, and 8 in that it includes only a single hemostatic valve.

Figure 20:
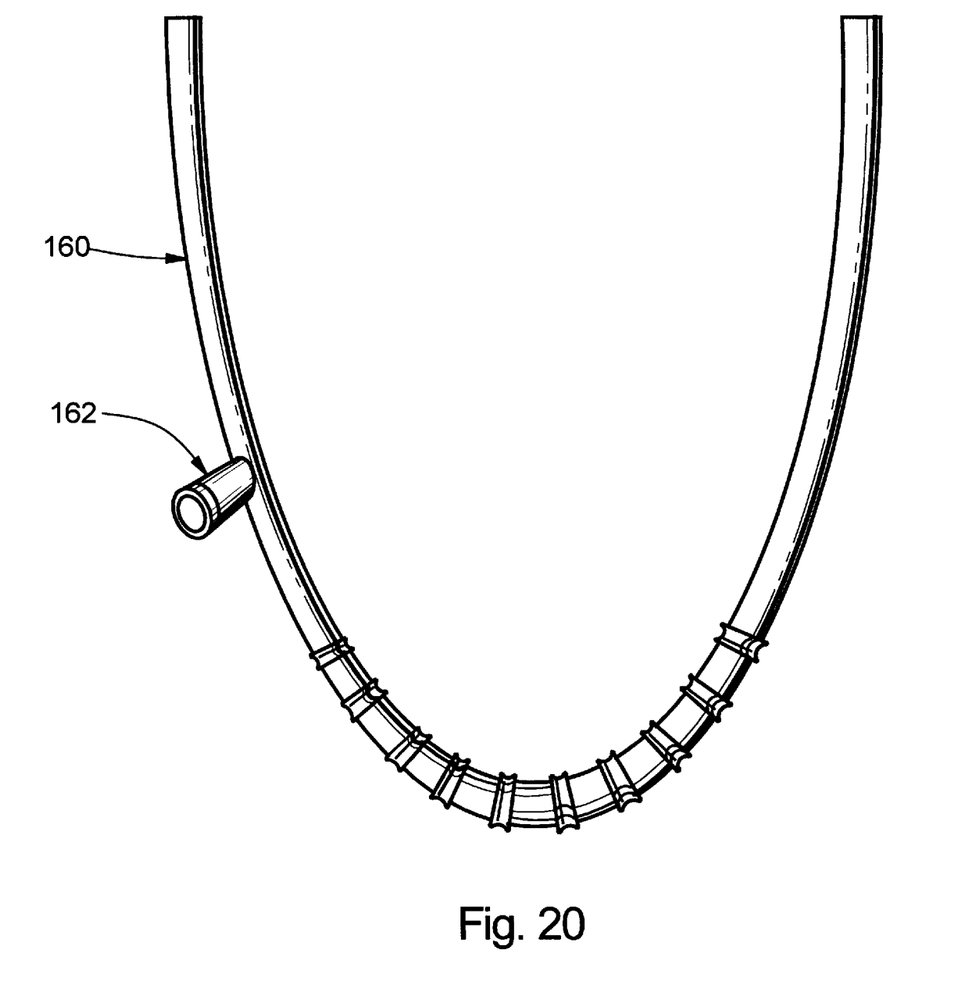
FIG. 20 is an illustration of a method and apparatus comprising a fourth embodiment of the invention.

Having reference to FIG. 20, there is shown an otherwise conventional graft 160 provided with a single surface access hemostatic valve constructed in accordance with the present invention. The graft 160 of FIG. 20 may be compared with the graft 94 of FIG. 10 wherein two access valves 96 and 98 each comprising the present invention are employed. It is important to realize that any of the surface access valves 96, 98, and 162 may be constructed as illustrated in FIG. 6, or as illustrated in FIGS. 7 and 8, or as illustrated in FIG. 18, depending upon the requirements of particular applications of the invention.

Figure 19:
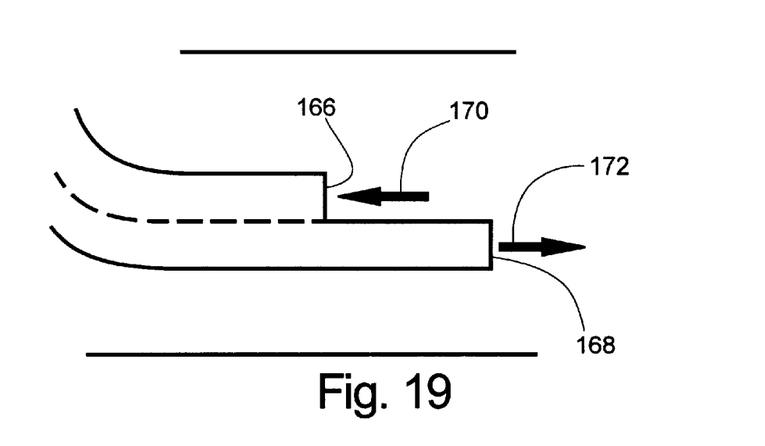
FIG. 19 is an enlargement of a portion of FIG. 18.

When a graft of the type illustrated in FIG. 10 and including two surface access valves comprising the present invention is employed, blood is normally withdrawn from the patient utilizing one of the surface access valves and is returned to the patient utilizing the other surface access valve. However, when a graft of the type illustrated in FIG. 20 comprising a single surface access valve incorporating the present invention is used, a double lumen catheter is employed to facilitate the withdrawal of blood and the return of blood through the same surface access valve. A double lumen catheter 164 is illustrated in FIGS. 18 and 19 and includes a first access port 166 and a second access port 168 for receiving and discharging blood as indicated by the arrows 170 and 172, respectively.

Figure 21:
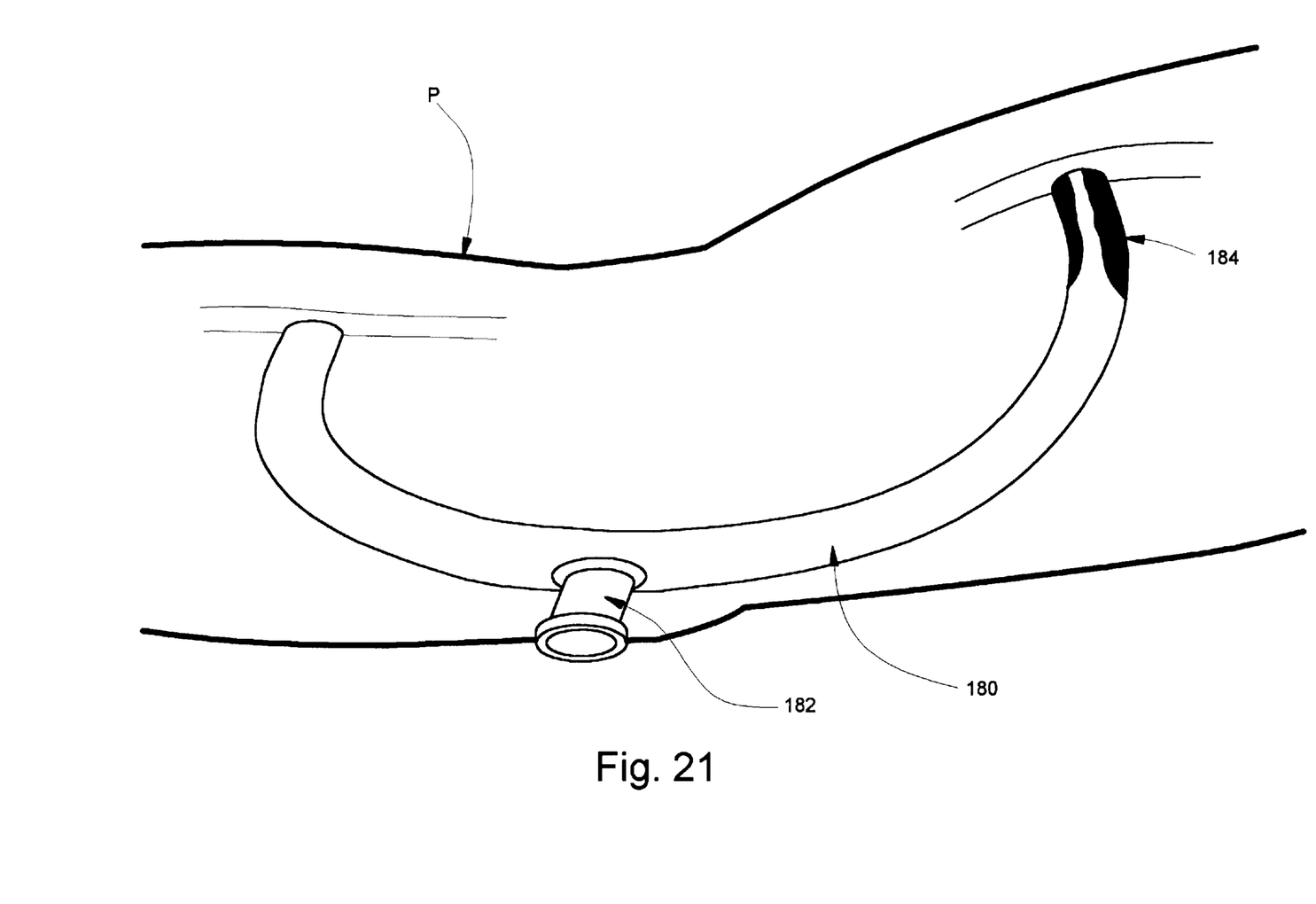
FIG. 21 is a diagrammatic illustration of a medical graft in which a blockage has occurred.
Figure 22:
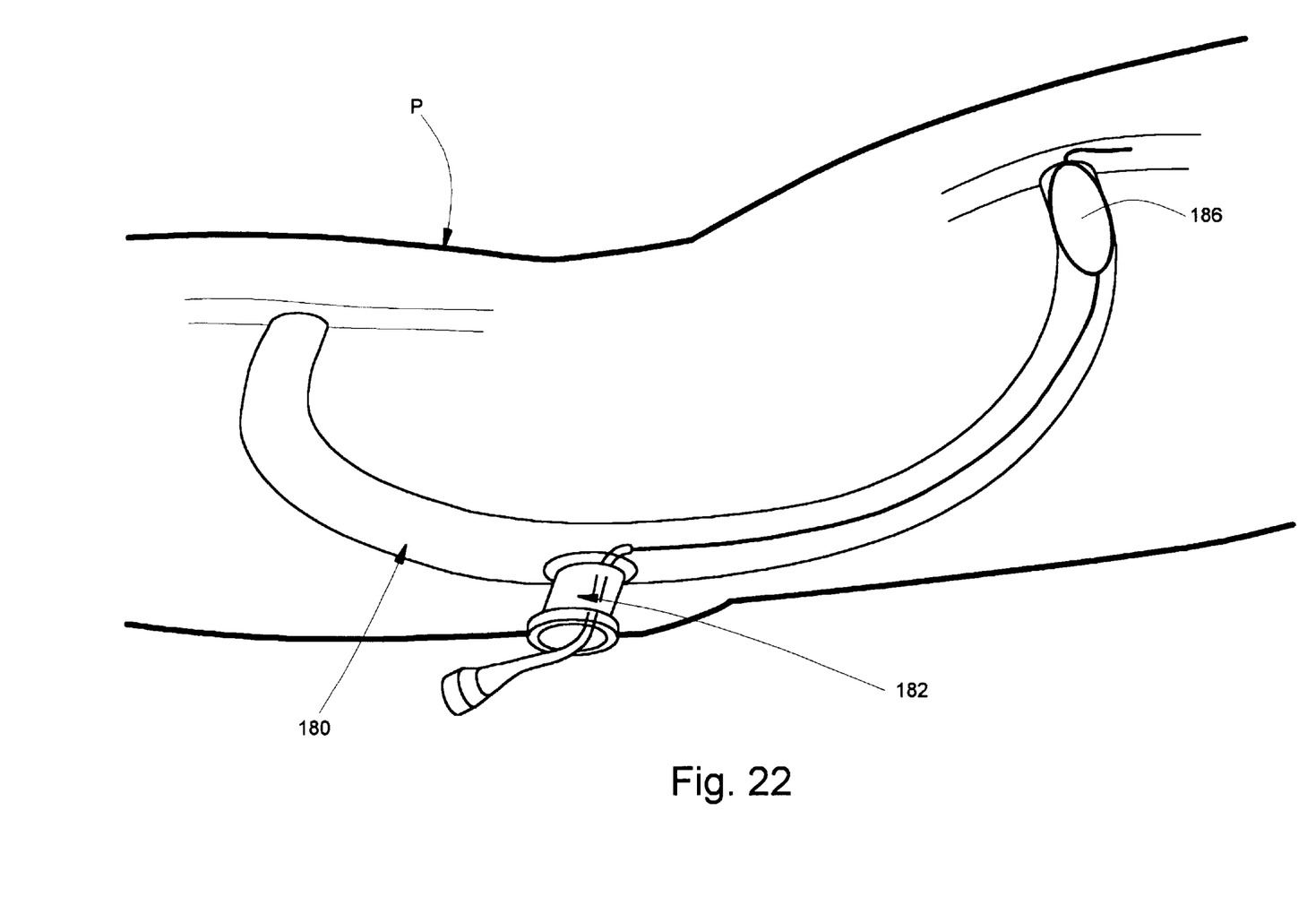
FIG. 22 is a diagrammatic illustration of a method of blockage removal utilizing the apparatus of the present invention.

FIGS. 21 and 22 illustrate the use of the surface access valve of the present invention for purposes beyond withdrawal of blood from and return of blood to a patient. An otherwise conventional graft 180 comprising an A-V fistula is provided with a surface access valve 182 incorporating the present invention. The graft 180 is implanted in a patient P and is connected between an artery and a vein thereof utilizing conventional techniques. As is often experienced in the use of grafts for hemodialysis and other medical procedures, a quantity of material 184 has accumulated in the graft 180 forming a thrombosis or clot which restricts the flow of blood through the graft 180.

As illustrated in FIG. 22, a catheter having a balloon 186 at the distal end thereof is inserted through the surface access valve 182 of the present invention and is positioned within the thrombosis or clot 184. The balloon 186 is initially inserted in the deflated condition, and after positioning within the thrombosis or clot 184 is expanded, whereby the material comprising the clot is compressed and forced outwardly to re-open the graft to permit the full flow of blood therethrough.

Although preferred embodiments of the invention have been illustrated in the accompanying Drawings and described in the foregoing Detailed Description, it will be understood that the invention is not limited to the embodiments disclosed, but is capable of numerous rearrangements, modifications, and substitutions of parts and elements without departing from the spirit of the invention.

I claim:

1. For use in the practice of medical procedures, a surface access double hemostatic valve comprising:

an elongate annular wall comprising a medical procedure graft;

a first hemostatic valve mounted in the wall of the graft;

a chamber surrounding the first hemostatic valve and extending outwardly therefrom to a distal end; and a second hemostatic valve mounted at the distal end of the chamber for positioning at the surface of the skin of the patient having the hemostatic valve installed therein;

the second hemostatic valve comprising a single thickness hemostatic valve;

the first hemostatic valve comprising a double thickness hemostatic valve; and wafers mounted on opposite sides of the first hemostatic valve.

* * * * *